United States Patent
Doubler et al.

(10) Patent No.: US 11,020,150 B1
(45) Date of Patent: Jun. 1, 2021

(54) POLYAXIAL BALL AND SOCKET FASTENER WITH A PRELOADED RING SET

(71) Applicant: Ortho Innovations, LLC, Palm Beach Gardens, FL (US)

(72) Inventors: Robert L. Doubler, Monroe, MI (US); John E. Hammill, Sr., Maumee, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/027,012

(22) Filed: Sep. 21, 2020

(51) Int. Cl.
  *A61B 17/70* (2006.01)
(52) U.S. Cl.
  CPC ...... *A61B 17/7037* (2013.01); *A61B 17/7032* (2013.01)
(58) Field of Classification Search
  CPC .................. A61B 17/70; A61B 17/7032–7046
  See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,483,334 A | 11/1984 | Murray |
| 4,693,240 A | 9/1987 | Evans |
| 4,708,510 A | 11/1987 | McConnell et al. |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,129,900 A | 7/1992 | Asher et al. |
| 5,133,717 A | 7/1992 | Chopin |
| 5,501,684 A | 3/1996 | Schlapfer et al. |
| 5,549,608 A | 8/1996 | Errico et al. |
| 5,569,247 A | 10/1996 | Morrison |
| 5,591,166 A | 1/1997 | Bernhardt et al. |
| 5,716,357 A | 2/1998 | Rogozinski |
| 5,800,435 A | 9/1998 | Errico et al. |
| 6,485,491 B1 | 11/2002 | Farris et al. |
| 6,672,788 B2 | 1/2004 | Hathaway |
| 6,716,214 B1 | 4/2004 | Jackson |
| 7,066,937 B2 | 6/2006 | Shluzas |
| 7,445,627 B2 | 11/2008 | Hawkes et al. |
| 7,942,909 B2 | 5/2011 | Hammill, Sr. et al. |

(Continued)

*Primary Examiner* — Eduardo C Robert
*Assistant Examiner* — Michelle C Eckman
(74) *Attorney, Agent, or Firm* — McHale & Slavin, P.A.

(57) ABSTRACT

A bottom loading fastening system that consists of the polyaxial ball and socket joint used in conjunction with an anchoring bone screw. The system allows attachment of a connector assembly to the anchoring bone screw having a spherical ball connector using a blocker ring preloaded with a split ring. Upon installation, the blocker ring and split ring are expanded into an expansion slot, causing relocation of said split ring into a lower groove, permanently attaching said connector assembly to said anchoring bone screw. The blocker ring having a counter-bored inner surface allowing said split ring to be preloaded to facilitate manufacturing. Dislodgement of the split ring from the blocker ring produces an audible and tactile indication that the sufficient force has been applied to lock the connector assembly to the bone screw.

7 Claims, 8 Drawing Sheets

(56) References Cited

U.S. PATENT DOCUMENTS

| | | | |
|---|---|---|---|
| 7,942,911 B2 | 5/2011 | Doubler et al. | |
| 7,947,065 B2 | 5/2011 | Hammill, Sr. et al. | |
| 7,951,173 B2 | 5/2011 | Hammill, Sr. et al. | |
| 8,075,603 B2 | 12/2011 | Hammill, Sr. et al. | |
| 8,197,518 B2 | 6/2012 | Hammill, Sr. et al. | |
| 8,465,065 B2 | 6/2013 | Browne et al. | |
| 8,465,530 B2 | 6/2013 | Hammill, Sr. et al. | |
| 8,663,291 B2 | 3/2014 | Doubler et al. | |
| 9,060,814 B2 | 6/2015 | Doubler et al. | |
| 9,615,858 B2 | 4/2017 | Doubler et al. | |
| 10,258,385 B1 | 4/2019 | Doubler et al. | |
| 10,285,738 B1 | 5/2019 | Doubler et al. | |
| 2015/0201972 A1* | 7/2015 | Doubler | A61B 17/7002 606/266 |
| 2017/0281241 A1* | 10/2017 | Jackson | A61B 17/7037 |
| 2020/0323563 A1 | 10/2020 | Rezach | |

* cited by examiner

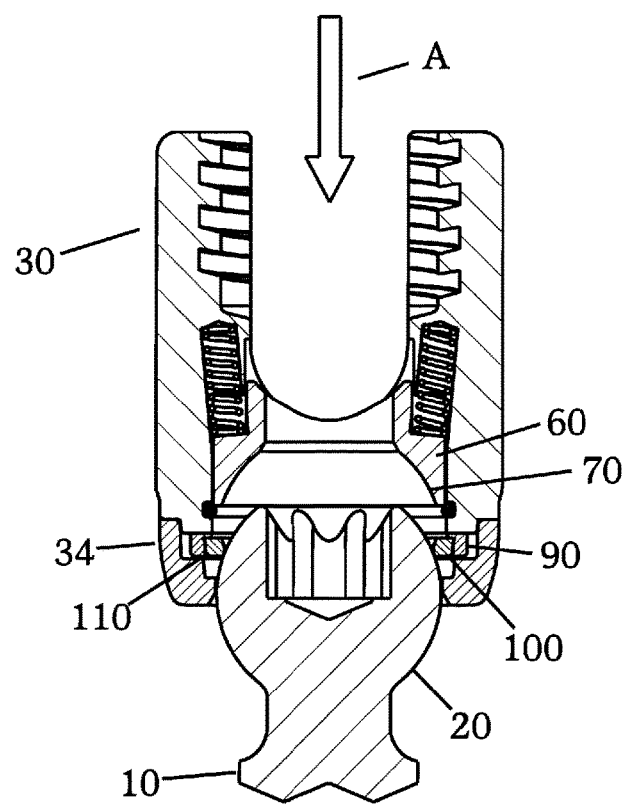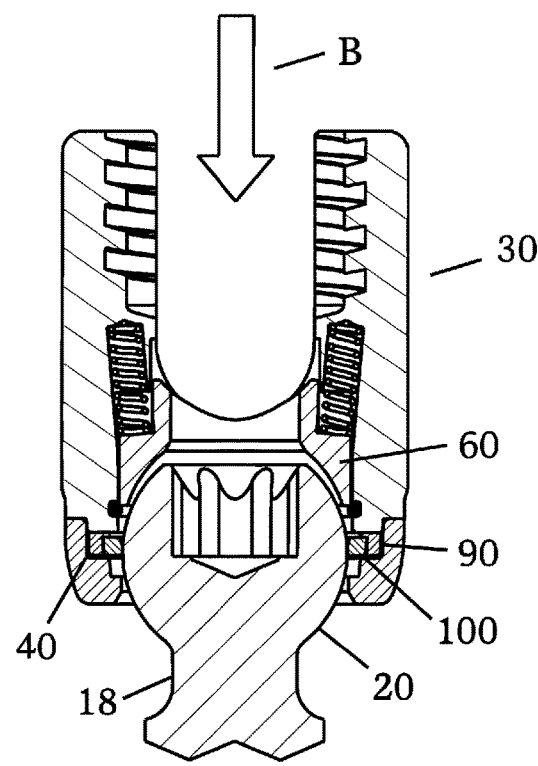
Fig. 15  Fig. 17
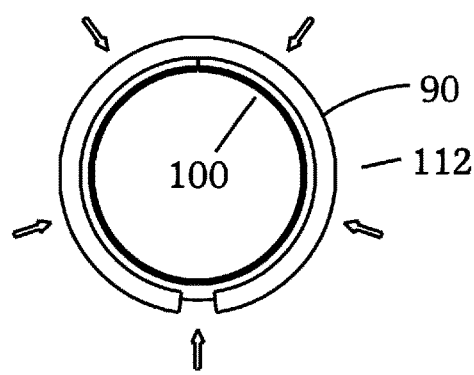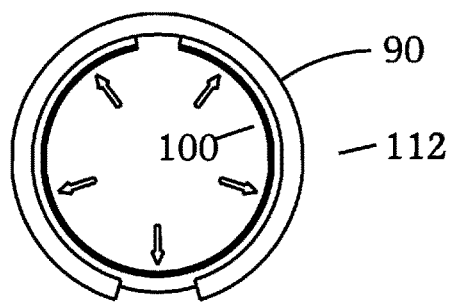
Fig. 16  Fig. 18

POLYAXIAL BALL AND SOCKET FASTENER WITH A PRELOADED RING SET

FIELD OF THE INVENTION

This invention is directed to the field of ball and socket fasteners, and in particular, to a polyaxial ball and socket fastener incorporating a preloaded ring set.

BACKGROUND OF THE INVENTION

In the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws with connectors are inserted into the patient's spinal bones and used to link the rods to stabilize the spine. A variety of designs exist, with each design addressing various aspects of the difficulties that arise when one re-shapes an individual's spine to follow a preferred curvature. Common to all spinal implant systems is the necessity for proper anchoring to the bone to provide support for the aforementioned components. While bone screws are commonly used for anchoring, the use of a polyaxial design has proven very effective in allowing a surgeon the flexibility to secure an installation with minimal strain on the individual.

A screw based device is located in bone structure and typically includes a polyaxial base with a connector member for securing a connecting rod. A situation that occurs during installation is that the condition of the bone structure needed to support the threaded shank of a screw cannot be determined until surgery has begun. Bone is not uniform in strength or position, requiring the surgeon to have access to a large inventory of various sized implants to be immediately available during every surgery. The surgeon must search through the inventory to locate the device required.

Once the implant combination is chosen, the anchoring screw may require angular insertion due to muscle structure or nerve locations. Any movement of muscle and other tissue increases the difficulty of the operation and can be a major trauma to the patient. Bone condition may also require oversized threads to achieve a suitable purchase to the bone. Consequently, the surgeon must maintain a large inventory of anchoring devices, or have a vendor standing by with a large inventory of anchoring devices that will hopefully meet the individual requirements. Bottom loading pedicle screw systems also reduce inventory allowing the use of various sized anchoring members for attachment to a connector assembly. The attachment to the connector assembly is a critical requirement which can employ a split ring that allows the spherical ball connector of an anchor to attach thereto. There are a number of configurations to employ the split ring. What is lacking in the art is a device that employs a counter-bored blocker ring that is limited to expansion with no vertical displacement, and is preloaded with a split ring.

Disclosures related to polyaxial pedicle screws are exemplified by the following patents; U.S. Pat. Nos. 7,066,937; 7,947,065; 8,075,603; 8,465,065; 6,485,491; 5,133,717; 5,129,900; 4,887,595; 4,946,458; 5,002,542; 4,854,304; 4,887,596; 4,836,196; 5,800,435; 5,591,166; 5,569,247; 5,716,357; 5,129,900; 5,549,608; 6,716,214; 6,565,567; 5,501,684; 4,693,240; 4,483,334; 4,273,116; 6,672,788; 4,708,510; 3,433,510; 7,445,627; 7,947,065; 7,942,911; 7,942,909; 7,951,173; 8,075,603; 8,197,518; 8,197,518; 8,465,530; 9,060,814; 10,258,385 and 10,285,738.

SUMMARY OF THE INVENTION

Briefly, the present invention is a bottom loading polyaxial ball and socket joint fixation system capable of a snap together assembly. The fixation system includes a threaded shank with a spherical ball connector on the opposite end of the threaded shank. The threaded shank is for anchoring to bone, and the spherical ball attaches to a connector assembly. The connector assembly includes a U-shaped upper connector member having a groove for receipt of a collar ring which maintains a saddle in position; and a lower connector member that is welded to the upper connector member, forming an upper cavity for receipt of a blocker ring preloaded with a split ring. A lower cavity is constructed and arranged to receive the split ring upon insertion of the spherical ball connector which displaces the split ring from the blocker ring. The upper cavity prevents the upward or downward displacement of the blocker ring, allowing only expansion along a horizontal plane. The lower cavity is arranged to receive the split ring in a fixed position, having an outer edge engaging the lower connector and an inner edge engaging the lower surface of the spherical ball. The lower cavity prevents movement of the split ring in a horizontal plane, and is prevented from vertical movement by the blocking ring, thereby forming an impermeable barrier for detachment of the spherical ball from the connector assembly. The use of the preloaded ring set, consisting of the blocker ring and the split ring, simplifies assembly in the manufacturing stage as the blocker ring includes a counter-bore for receipt of the split ring.

In operation, a threaded shank end of an anchoring member is attached to bone, and a spherical ball located on the opposite end is receptive to a connector member. The spherical ball connector is inserted through an aperture in the lower connector of the connector assembly, and the spherical ball contacts the split ring that is preloaded into the blocker ring. The split ring forces the blocker ring horizontally into an upper cavity, allowing the spherical ball connector to pass. The split ring has a sloped inner edge that engages the lower surface of the spherical ball, dislodges the split ring from the blocker ring, and causes displacement of the split ring to the lower cavity. The lower cavity has a side wall that prevents expansion of the split ring, and the split ring is prevented from upward movement by the blocker ring, thereby causing permanent attachment of the connector assembly to the anchoring member. A set screw can then be utilized to press a connecting rod into contact with a saddle placed over the spherical ball, simultaneously causing the lower portion of the spherical ball connector to wedge against the inner surface of the split ring, immobilizing the connection. In the preferred embodiment, the saddle employs compression springs to keep the connector assembly in position during installation. This allows a surgeon to easily move the connector assembly into a selected position and the angular position of the connector assembly will remain the same to facilitate installing of connecting rods. The system is modular, employing a collection of anchoring assemblies that are linked, via various connectors, to strategically arranged stabilizing rods. The connector assemblies are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a bottom loading polyaxial ball and socket fastener for use in a spinal stabilization system utilizing a preloaded ring set consisting of a blocker ring expanded by a split ring, allowing ease of assembly.

Another objective of the invention is to disclose the use of a polyaxial ball and socket system that is capable of securing various anchors to various connector members so as to reduce the amount of inventory required to meet a particular installation.

It is an additional objective of the present invention to provide a bone screw assembly that includes a split ring locking mechanism that is simple, strong and reliable; wherein a blocker ring is preloaded with a split ring and, once the split ring is detached from the blocker ring, the split ring is held in place by an interference fit beneath the blocker ring in a predefined cavity, and the blocker ring is unable to be moved in a vertical direction.

Another objective of the invention is to teach the use of a retainer ring formed from a 360-degree ring that is released from a blocker ring when the spherical head of a screw is forced through the retainer ring during assembly. The dislodgement of the split ring from the blocker ring is permanent, and the spherical head of the screw cannot be removed from the connector assembly.

Another objective of the invention to provide a spinal fixation system that has an audible sound and tactile feel when the spherical ball causes the split ring to release from the blocker ring.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE DRAWINGS

FIG. 15 is a cross sectional view illustrating the anchoring member engaging the split ring;
FIG. 16 is a cross sectional view illustrating the anchoring member passing the split ring;
FIG. 17 is a top plane view illustrating compression of the ring set;
FIG. 18 is a top plane view illustrating expansion of the ring set.

DETAILED DESCRIPTION OF THE PREFERRED EMBODIMENT

Figure 1:
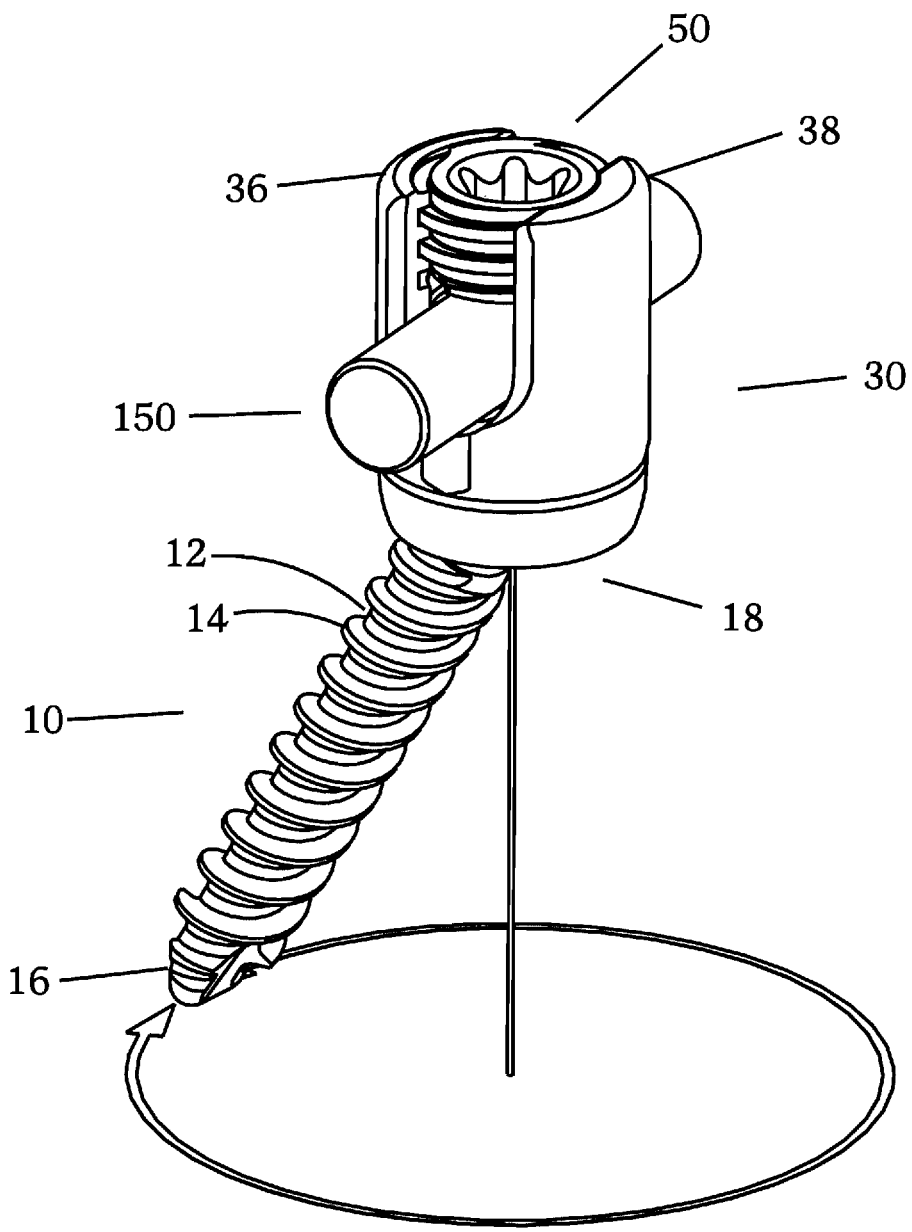
FIG. 1 is a perspective view of a screw assembly shown locked with a rod and tilted to a maximum axial angle.
Figure 2:
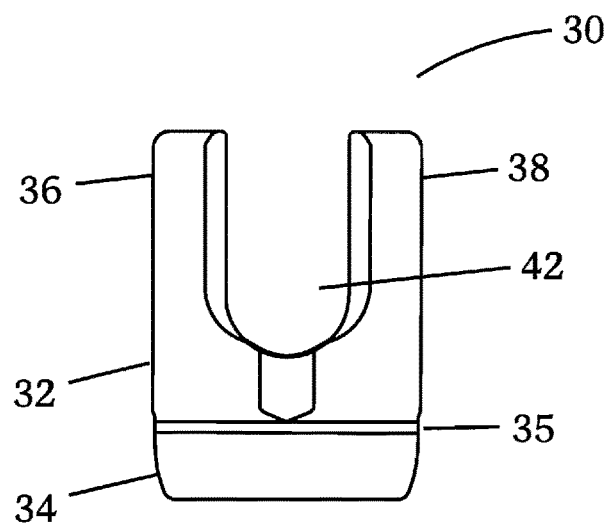
FIG. 2 is a side view of the connector assembly.
Figure 3:
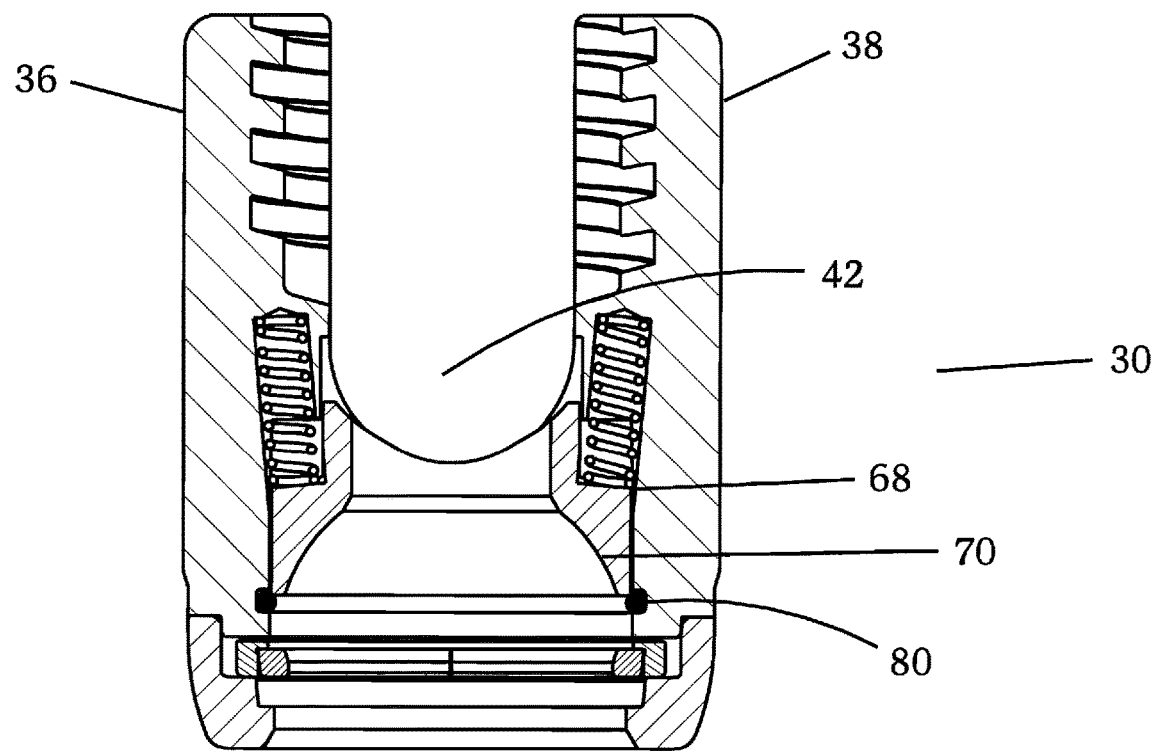
FIG. 3 is a cross sectional side view of FIG. 2.
Figure 4:
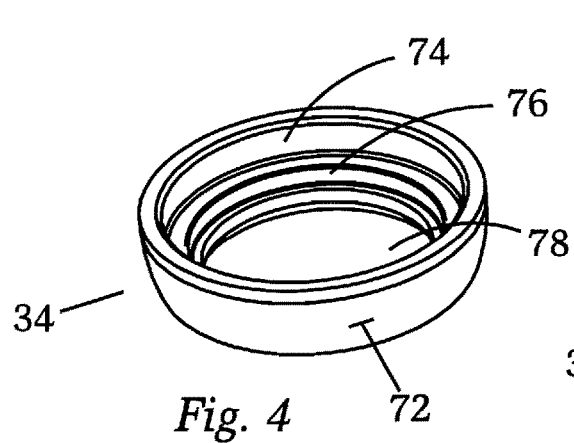
FIG. 4 is a perspective view of the lower connector member.
Figure 5:
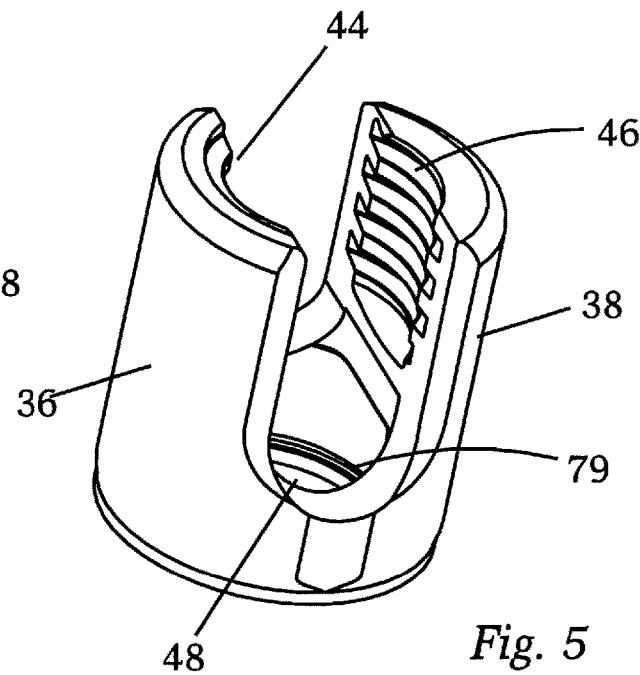
FIG. 5 is a perspective view of the upper connector member.
Figure 6:
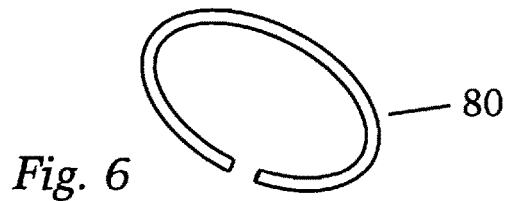
FIG. 6 is a perspective view of the retainer ring.
Figure 7:
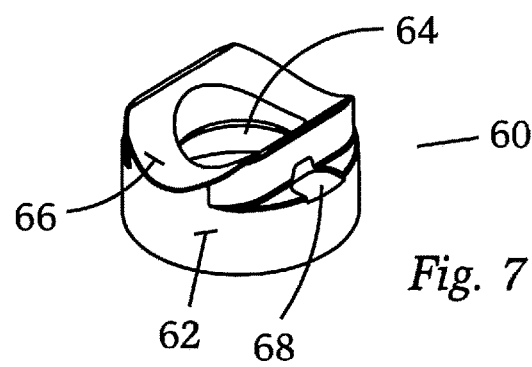
FIG. 7 is a perspective view of the saddle.
Figure 8:
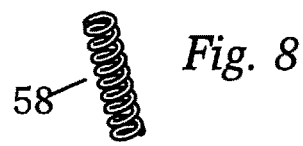
FIG. 8 is a perspective view of the compression spring.
Figure 9:
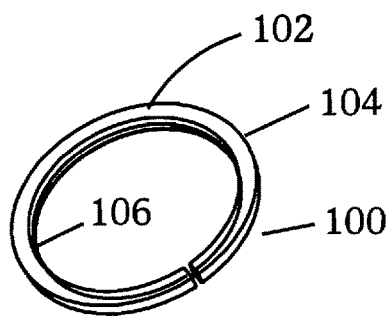
FIG. 9 is a perspective view of the split ring.
Figure 10:
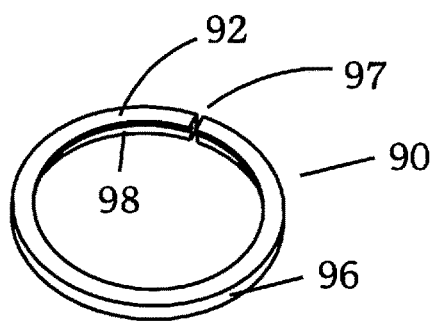
FIG. 10 is a perspective view of the blocker ring.
Figure 11:
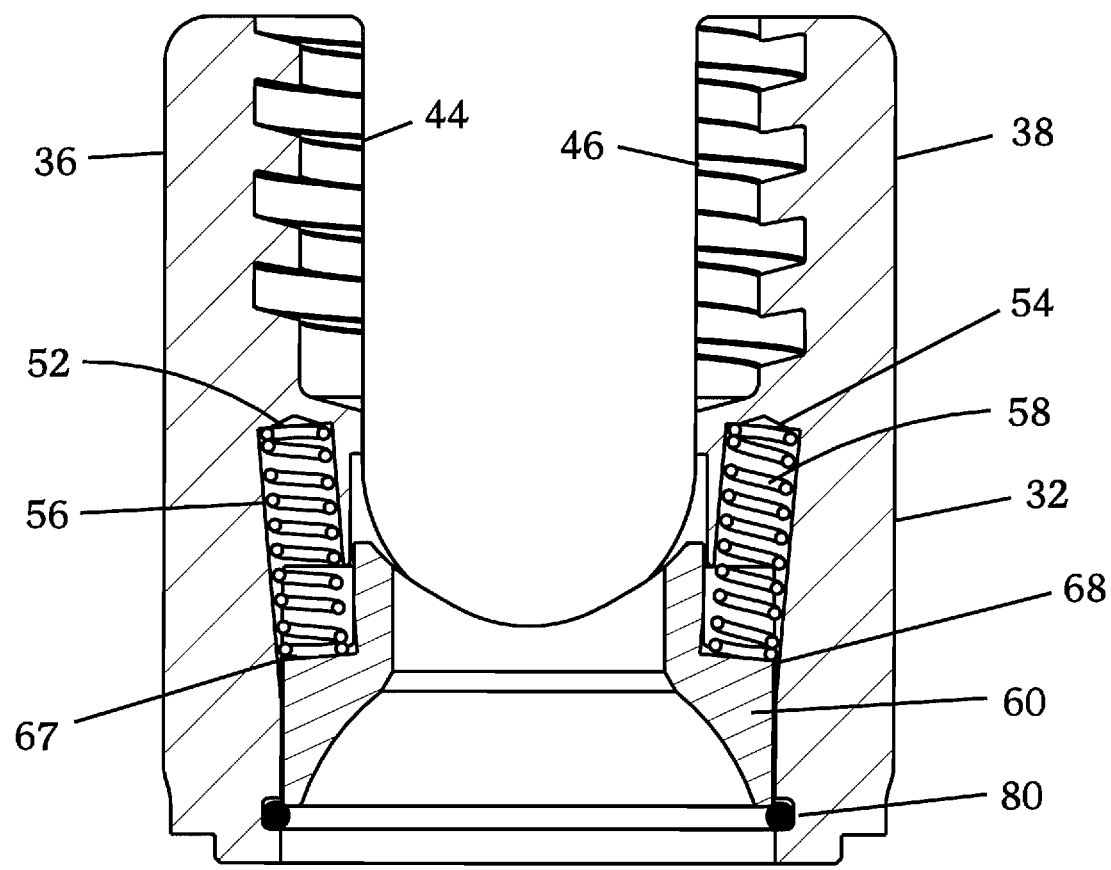
FIG. 11 is a cross sectional view of the connector assembly.
Figure 12:
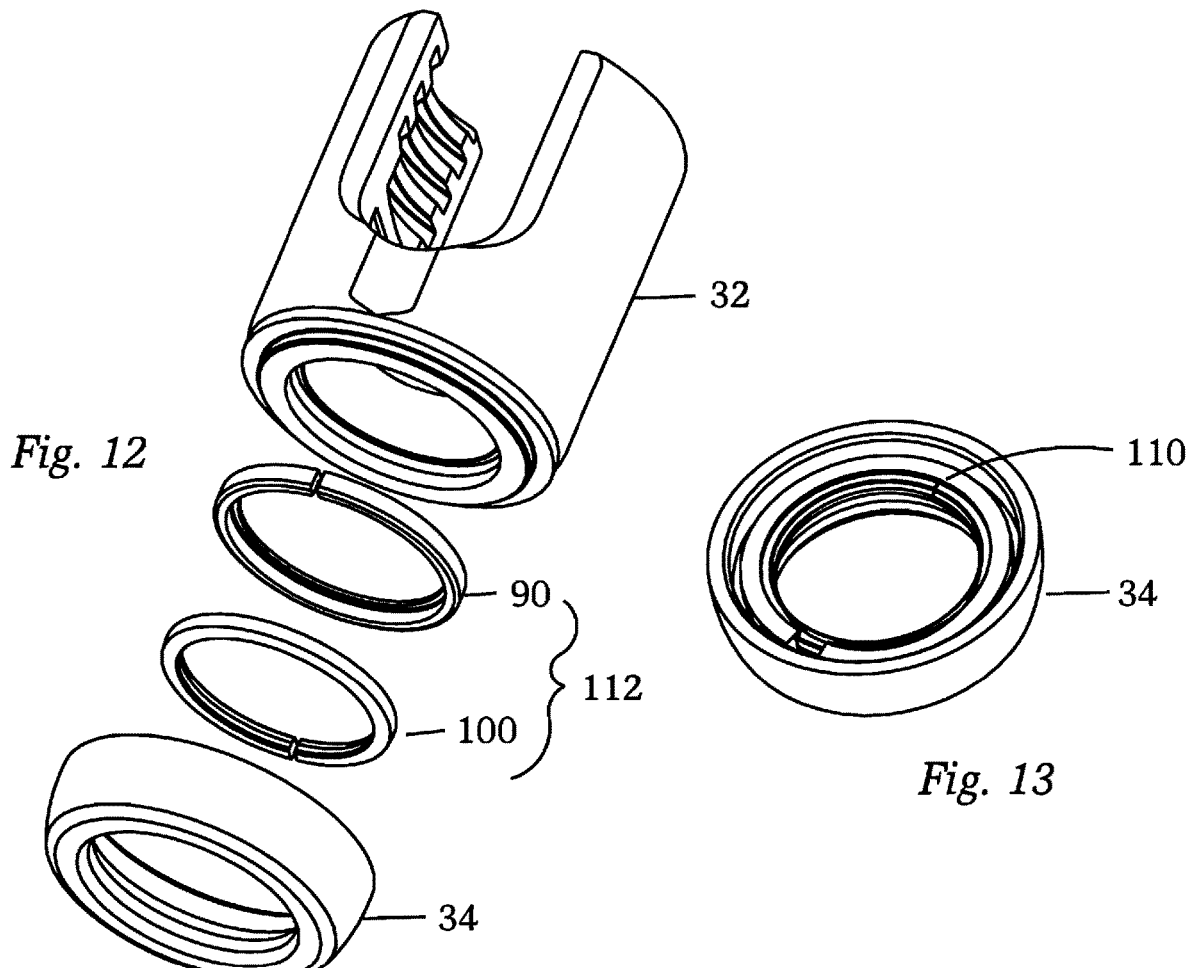
FIG. 12 is an exploded view of the connector assembly.
Figure 13:
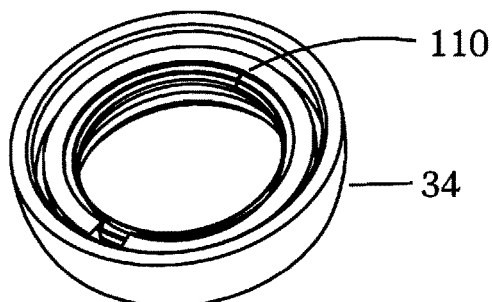
FIG. 13 is a perspective view of the lower connector member with the ring set installed.
Figure 14:
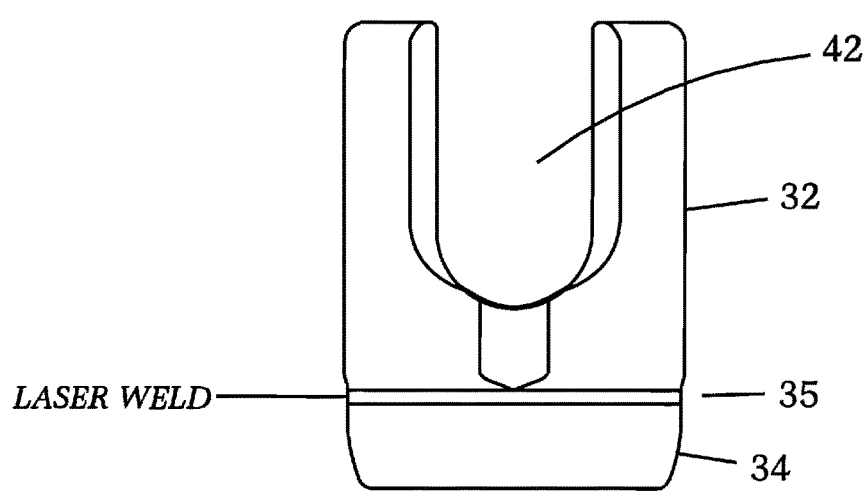
FIG. 14 is a side view of the connector assembly depicting weldment position.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the polyaxial ball and socket fastening system adapted for use in a spinal fixation system. The fastening system includes an anchor member (10) formed from a shank (12) having bone threads (14) formed along a first end (16). It is important to note that the proportions of the anchor member (10) depicted are for illustrative purposes only and variations in the length of the shank, diameter of the screw, thread pitch, thread length, number of thread leads, shank induced compression and the like may be varied without departing from the scope of the invention. At the upper end (18) of the shank (12) is a ball shaped spherical ball connector (20) having a predetermined diameter. A driver receptacle (22), which may be configured as a plurality of recesses or a single recess for an insertable driver tool, is located along the top of the spherical ball connector (20) for use in installing the anchor member (10) by use of a driving tool. It should be noted that the driver receptacle (22) may be any shape, male or female, suitable for cooperation with a driving tool to rotate the anchor member (10) into its final position.

A connector assembly (30) is securable to the anchor member (10; the connector assembly (30) including an upper connector member (32) to be attached to a lower connector member (34) by a weldment (35). Upon attachment by the weldment (35), the upper connector member (32) and the lower connector member (34) form an expansion slot (40) therebetween. The upper connector member (32) is further defined by a first side wall (36) and a second side wall (38) forming a U-shaped opening (42). The first side wall (36) has threads (44) along an upper portion thereof, with cooperating threads (46) placed along an upper portion of the second side wall (38). A centrally disposed passageway or aperture (48) of a first diameter permits insertion of the driving tool, not shown, for use in mounting the anchor member (10) by engaging of the driver receptacle (22). A set screw (50) is operatively associated with the threaded side walls (36) and (38). The upper connector member (32) includes first and second compression spring sockets (52, 54) positioned on each side of the aperture (48) for receipt of compression springs (56) and (58). It should be noted that while the compression springs (56) and (58) are illustrated as coil springs, any spring or resilient type member suitable for displacing the saddle component may be utilized without departing from the scope of the invention. Such springs or resilient members may include, but should not be limited to, Belleville type springs, leaf springs, polymeric members, and suitable combinations thereof.

Figure 22:
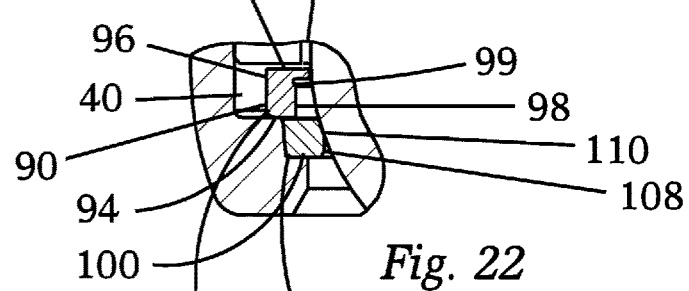
FIG. 22 is an enlarged view depicting final ring placement.

A saddle (60) having a cylindrical sidewall (62) with a centrally located aperture (64) is slidably insertable into the upper connector member (32). An upper surface (66) of the saddle (60) is concave shaped for receipt of a connection rod (150), shown in FIG. 1, with support ledges (67 and 68) positioned on each side of the concave shaped upper surface (66). A lower surface (70) of the saddle (60) is spherical shaped and coincides with the shape of the spherical ball (20). The upper surface (66) of the saddle (60) provides additional surface area for contact with the connecting rod (150) and may include a knurled or otherwise modified surface finish adapted to enhance gripping power between the rod and the connector member. The saddle (60) is constructed and arranged to cooperate and frictionally engage the spherical ball (20) to prevent movement of the anchor member (10) in relation to the connector assembly (30) when fully assembled. The lower connector (34) is defined by a continuous side wall (72) having an inner surface with an upper recessed wall (74) forming the expansion slot (40), illustrated in FIG. 22, with a groove (76) positioned beneath the upper recessed wall (74). The lower connector (34) also has a centrally disposed aperture (78) for receipt of the spherical ball connector (20) into the saddle (60) lower surface (70), as will be further explained. A groove (79) formed in the upper connector (32) receives a retainer ring (80) for securing the saddle (60) to the upper connector member (32).

A blocker ring (90) is constructed and arranged to fit within the expansion slot (40); the blocker ring (90) having a top wall (92), a bottom wall (94), a non-continuous outer side wall (96) having a break (97) with a corresponding inner side wall (98) having an upper surface (99) forming an inverted L-shape. The inner side wall (98) is a counter-bored surface (93) for receipt of a split ring (100). The split ring (100) is preloaded into the blocker ring (90), the split ring (100) having a top surface (102), a non-continuous outer side wall (104) with a corresponding inner wall (106) having a beveled edge (108) formed along a lower portion and a chamfer surface (110) formed along an upper portion, the outer side wall (104) of the split ring (100) engaging the counter-bore surface (93) of the inner side wall (98) of the blocker ring (90), allowing for ease of assembly. The blocker ring (90) and the split ring (100) forming a ring set (112).

The spherical ball (20) is inserted through the aperture (78) in the lower connector (34) of the connector assembly (30). The spherical ball (20) contacts the split ring (100) that is preloaded into the blocker ring (90). The split ring (100) forces the blocker ring (90) horizontally into the expansion slot (40), allowing the spherical ball connector (20) to pass. The split ring (100) beveled edge (108) engages the surface of the spherical ball (20) which dislodges the split ring (100) from the blocker ring (90), causing displacement of the split ring (100) into the groove (76). The groove (76) side wall prevents expansion of the split ring (100), and the split ring (100) is prevented from upward movement by the blocker ring (90) lower surface (94), thereby causing permanent attachment of the connector assembly (30) to the anchoring member (10). The set screw (50) can then be utilized to press the connecting rod (150) into contact with the saddle (60) placed over the spherical ball (20), simultaneously causing the lower portion of the spherical ball connector (20) to wedge against the inner surface of the split ring (100), immobilizing the connection. In the preferred embodiment, the saddle (60) employs compression springs (56) and (58) to keep the connector assembly (30) in position during installation. This allows a surgeon to easily move the connector assembly (30) into a selected position, and the angular position of the connector assembly (30) will remain the same to facilitate installing of connecting rods (150). The system is modular, employing a collection of anchoring assemblies that are linked, via various connectors, to strategically arranged stabilizing rods. The connector assemblies are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

The material of the blocking ring (90) and split ring (100), together with the expansion slot (40), provides a biasing force that ensures that the rings will not bend as the spherical ball connector (20) passes. After the spherical ball connector (20) has been captured by the split ring (100), the split ring (100) will thereafter serve to maintain a slight upward force on the spherical ball connector (20) as the split ring (100) attempts to contract. The split ring (100) provides a tactile feel, wherein the ring snaps into position to indicate proper installation.

Unique to this invention is the ability to lock both the blocker ring (90) and the split ring (100) into a position that prevents detachment of the spherical ball connector (20) from the connector assembly (30). This further allows a surgeon to attach various types of anchor members or the like to the connecting assembly, after having installed the bone anchor into the bone of a patient. While there are a myriad of anchoring devices that can be adapted to include the spherical ball, bone hooks, etc., for ease of illustration, the bone screw is depicted. It is well known that various lengths and diameters of bone screws are available, many of which would not fit through the inner diameter of the connector assembly. Thread styles, lengths and so forth that are best suited for installation may be estimated before surgery, but it is well known that only during actual surgery can the proper style be confirmed. Because it is most difficult to predict the proper combination of anchor screw and connector member, surgeons must either have a large selection of spinal implants to choose from or be forced to use the closest combination and hope that it will suffice.

Referring to FIG. 15, the connector assembly (30) is illustrated by arrow (A) illustrating placement of the connector assembly (30) over the spherical ball connector (20) of the anchor member (10). In this position, the blocker ring (90) and split ring (100) are in a preloaded ring set (112), configuration as illustrated in FIG. 16. The spherical ball connector (20) is passing through the aperture (78) of the lower connector (34). Referring to FIG. 17, the connector assembly (30) is illustrated by arrow (B) illustrating placement of the connector assembly (30) over the spherical ball connector (20) of the anchor member (10). In this position, the blocker ring (90) and split ring (100) are expanded, also illustrated in FIG. 18, outwardly into the expansion slot (40). The spherical ball connector (20) is passing through the ring set (112) by pressing against the split ring (100), which in turn pushes out blocker ring (90).

Figures 19, 21:
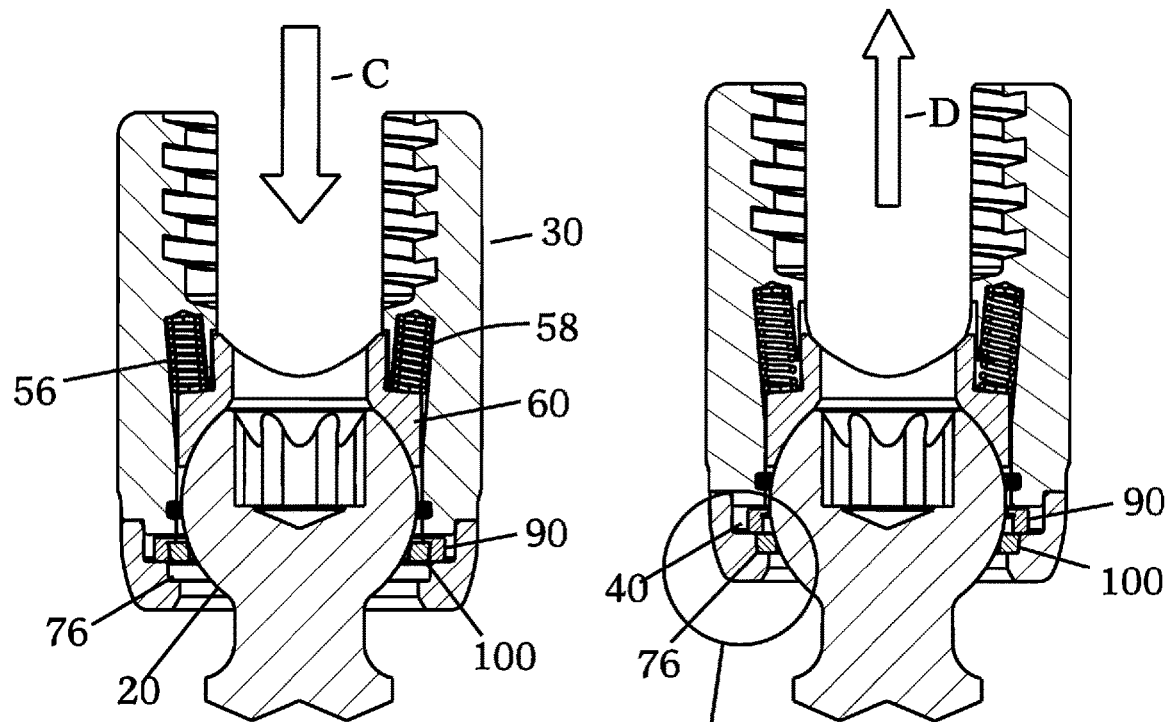
FIG. 19 is a cross sectional view illustrating the anchoring member in a position past the split ring.
FIG. 21 is a cross sectional view illustrating the anchoring member having dislodged the split ring into the groove.
Figures 20, 23:
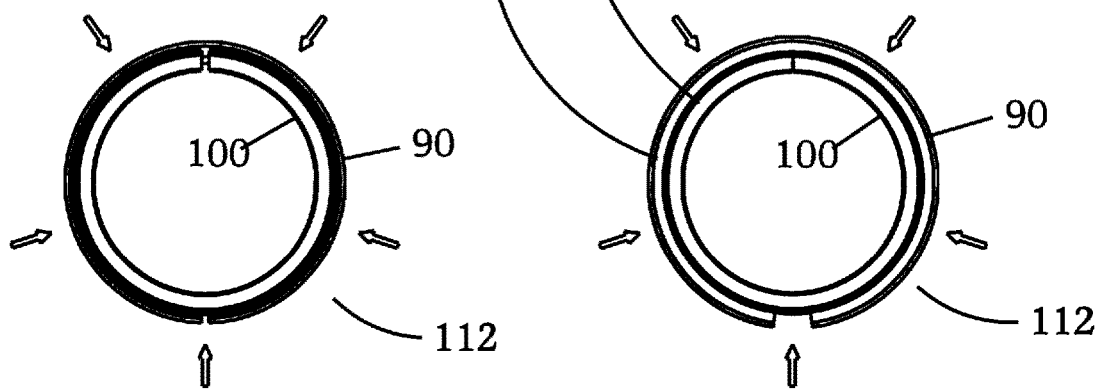
FIG. 20 is a top plane view illustrating the split ring fitting within the blocker ring.
FIG. 23 is a top plane view illustrating positioning of the blocker ring and the split ring.
Figure 24:
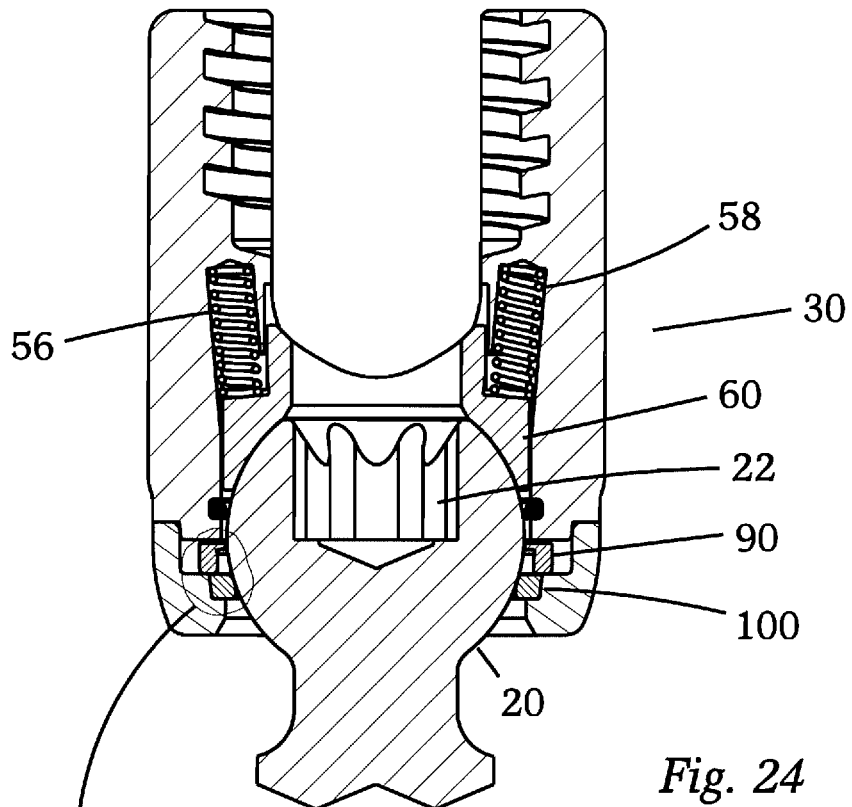
FIG. 24 is a cross sectional view of the spherical ball connector engaged by the connector assembly.
Figure 25:
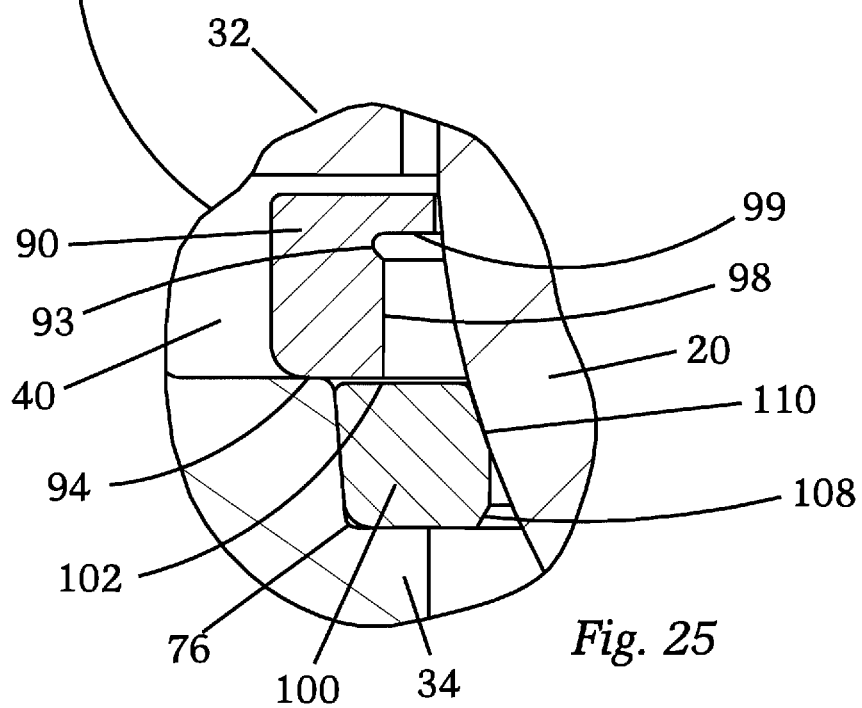
FIG. 25 is an enlarged cross sectional view of the blocker ring and split ring depicted in FIG. 24.

Referring to FIG. 19, the connector assembly (30) is illustrated by arrow (C) illustrating placement of the connector assembly (30) over the spherical ball connector (20) with the widest surface of the spherical ball connector (20) passing the split ring (100); the spherical ball connector (20) causing the compression of springs (56, 58) with the movement of the saddle (60). In this position, the ring set (112) is beneath the outer circumference of the spherical ball (20) and pressing inwardly, as illustrated in FIG. 20.

Referring to FIGS. 21-25, the connector assembly (30) is illustrated by arrow (D) illustrating the completion of the coupling of connector assembly (30) over the spherical ball connector (20); the spherical ball connector (20) causing dislodgement of the split ring (100) from the blocker ring (90) into the groove (76). The blocker ring (90) is positioned against the spherical ball (20) with the L-shape causing directional placement. The split ring (100) is now in groove (76) and is blocked from any movement by the blocker ring (90), thereby preventing detachment of the spherical ball connector (20) from the connector assembly (30). The saddle (60), engaging the spherical ball connector (20) with the springs (56, 58), provides a biasing force to keep the connector assembly (30) in a position selected by the surgeon while connecting rods and fasteners are attached.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A polyaxial ball and socket fastener comprising:
   an anchor member formed from a shank having bone threads formed along a first end and a spherical ball connector formed along a second end thereof;
   a connector assembly securable to said anchor member, said connector assembly including an upper connector member welded to a lower connector member arranged to form an expansion slot therebetween, said upper connector member further defined by a first side wall and a second side wall forming a U-shaped opening with threads along an upper portion of said first and second side walls, said upper connector having a top end and a bottom end with a centrally disposed passageway of a first diameter, said lower connector member including a lower groove juxtapostioned to said expansion slot;
   a set screw operatively associated with said threaded side walls of the first and second side walls;
   a saddle slidably insertable into said passageway, said saddle having an upper U-shaped surface in alignment with said U-shaped opening and a lower spherical surface for receipt of said spherical ball connector, said saddle secured to said upper connector by a retainer ring;
   a blocker ring positioned within said expansion slot, said blocker ring having a top wall, a bottom wall, a non-continuous outer side wall with a corresponding inner side wall having an upper surface;
   a split ring preloaded into said blocker ring, said split ring having a top surface, a non-continuous outer side wall with a corresponding inner wall having a beveled edge formed along a lower portion and a chamfer surface formed along an upper portion, said non-continuous outer side wall of said split ring engaging said inner side wall of said blocker ring;
   wherein said bottom end of said connector assembly is positioned over said spherical ball connector of said anchored member, said blocker ring and split ring expands into said expansion slot to permit passage of said spherical ball connector, whereby said split ring is disengaged from said blocker ring and forced into said lower groove beneath said blocker ring, wherein said split ring engages said spherical ball connector.

2. The polyaxial ball and socket fastener according to claim 1, wherein said beveled edge of said split ring is constructed and arranged to allow the upper portion of said spherical ball connector to pass said split ring by expanding said split ring and blocker ring into said expansion slot for attachment to said connector assembly.

3. The polyaxial ball and socket fastener according to claim 1, wherein said chamfered edge of said split ring is constructed and arranged to allow the lower portion of said spherical ball connector to dislodge said split ring from said blocker ring, wherein said split ring is moved into said lower groove, said chambered edge of said split ring engaging a lower portion of said spherical ball connector to prohibit removal from said connector assembly.

4. The polyaxial ball and socket fastener according to claim 1, wherein said inner surface of said blocker ring is a counter-bored surface for receipt of said non-continuous outer wall of said split ring, said counter-bored surface allowing said split ring to be retained by said blocker ring to facilitate assembly.

5. The polyaxial ball and socket fastener according to claim 1, wherein said blocker ring expands when said spherical ball connector is installed, causing said split ring to release said blocker ring, said split ring moved into said lower groove with a portion of said top surface of said split ring positioned beneath a portion of said bottom surface of said blocker ring.

6. The polyaxial ball and socket fastener according to claim 1, wherein said split ring is constructed and arranged to indicate a change in diameter by tactile feel and sound when the split ring is released from said blocker ring.

7. The polyaxial ball and socket fastener according to claim 1, wherein said saddle has a generally spherical lower surface to be complimentary to the upper portion of said spherical ball connector, and an upper surface to be complimentary of said U-shaped opening for engagement with a rod connector.

* * * * *